United States Patent [19]

Kurland

[11] Patent Number: 4,686,972
[45] Date of Patent: Aug. 18, 1987

[54] SURGICAL DEFLECTOR AND DRILLING GUIDE

[76] Inventor: Kenneth Z. Kurland, 2 W. McCabe Rd., El Centro, Calif. 92243

[21] Appl. No.: 857,341

[22] Filed: Apr. 30, 1986

[51] Int. Cl.$^4$ .............................................. A61F 5/04
[52] U.S. Cl. ............................ 128/92 V; 128/92 VD; 128/20
[58] Field of Search ............ 128/92 XV, 92 R, 92 V, 128/92 VZ, 92 YG, 92 VY, 92 YV, 92 YZ, 92 VD, 20, 305, 304; 7/166

[56] References Cited

U.S. PATENT DOCUMENTS

| D. 245,918 | 9/1977 | Shen | 128/92 VD |
|---|---|---|---|
| 659,182 | 10/1900 | Pilling | 128/20 |
| 4,621,630 | 11/1986 | Kenna | 129/92 VD |

FOREIGN PATENT DOCUMENTS

| 0963517 | of 1983 | U.S.S.R. | 128/20 |
|---|---|---|---|
| 1060177 | of 1983 | U.S.S.R. | 128/20 |

OTHER PUBLICATIONS

Plastic and Reconstructive Surgery, "Ideas and Innovations," by John W. Devine, Jr., M.D., & Ralph Millard, M.D. 1971.
Murray Baumgartner Surgical Instrument Company Sales Catalog, 12/26/1934.
"Treatment of Fracture of the Neck of the Femur" by E. T. Bailey, M.D. 2/13/1937.
"Instruments of Surgery" Francis-Mitchell-Heggs and H. Guy Radcliff Drew, 1963, William-Hiendmann Medical Books.

Primary Examiner—C. Fred Rosenbaum
Assistant Examiner—Ralph Lewis
Attorney, Agent, or Firm—Charmasson & Holz

[57] ABSTRACT

A surgical deflector or boring tool positioner specifically designed to help orthopedic surgeons in gaining access to hard-to-reach parts of a patient's anatomy and for guiding a drill bit, awl or reamer into a bone. The tool combines a curved blade and a triangular handle. The curved blade is terminated by an arcuate indentation designed to seat on a bone. The triangular handle doubles as a muscle deflector. One of a series of boring guides can be mounted on the blade to direct the tip of the boring tool into the bone at a desired angle. A fiber-optics light may be clipped to the shank of the tool to illuminate the work area.

3 Claims, 4 Drawing Figures

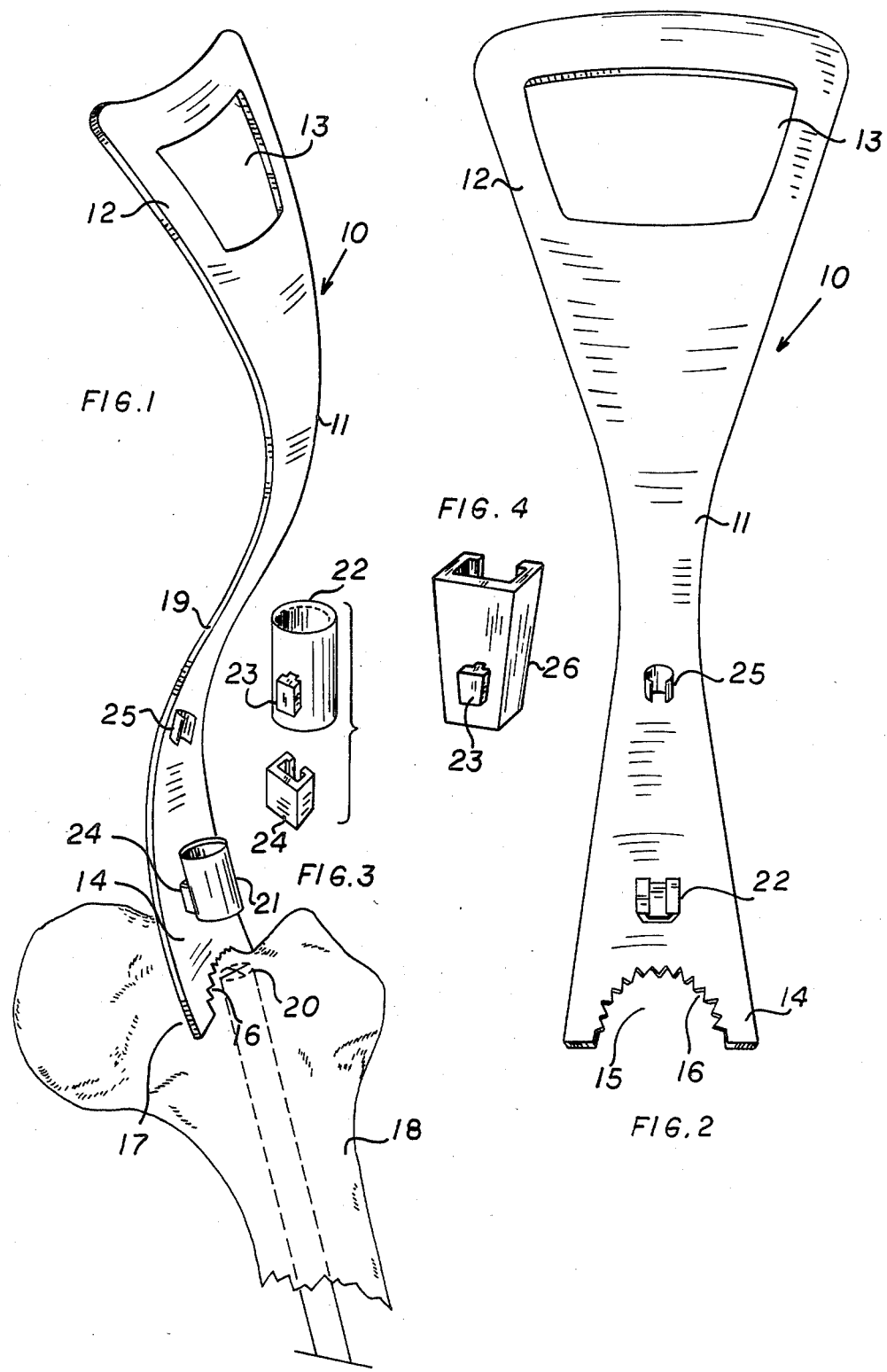

SURGICAL DEFLECTOR AND DRILLING GUIDE

FIELD OF THE INVENTION

This invention relates to medical instruments and more specifically to a surgical femoral deflector and drilling guide.

BACKGROUND OF THE INVENTION

One common method of fixing fractured bones and more specifically femurs is the insertion of a pin along the shaft of the femur.

To perform such surgical insertion, a perforation needs to be drilled throughout the femur. The basic problem facing the surgeons in the field is in starting to drill a hole in the neck of the bone or femur.

The normal existing procedure is to cause an incision in the thigh, through which a surgeon inserts his fingers and gropes for the proper target point on the neck of the femur. Once this point is located, the surgeon inserts a drill through the incision to start an initial perforation or hole.

The process as described above is not accomplished without severe problems. It could prove to be bothersome and painful to the patient, as well as time consuming and frustrating to the surgeon.

The difficulty arises from several factors. The first is the slippery nature of the bone, which causes the drill to slip away from the initial target point of perforation.

The second adverse factor is the inconvenience of having to deflect tendons and muscles covering the bone to gain a prolonged and unobstructed access to its neck.

The third adverse factor is the widely differing structure of the patient's hips and his level of adiposis. The heavier the patient, the more difficult it is for the surgeon to gain access to the neck of the femur.

The fourth adverse factor is the lack of illumination for guiding a drill or other medical instruments during the surgery.

Wherefore there is a basic need for a medical device which addresses and resolves the above difficulties or problems.

SUMMARY OF THE INVENTION

The above stated need is provided for by the present invention whose primary and secondary objects are:
  to provide a retractor equipped with a positioner which firmly positions the retractor on the bone;
  to provide a deflector for uncovering the bone to be drilled or worked upon; and
  to provide a guide for the drill, fiber optic means of illumination, or other medical instruments to be used during surgery.

These and other objects are achieved by the surgical defector and drilling guide as disclosed herein.

BRIEF DESCRIPTION OF THE DRAWINGS

FIG. 1 is a perspective view of the preferred embodiment shown riding against the head of a patient's femur;

FIG. 2 is a front elevational view of the embodiment shown without the boring-tool guide;

FIG. 3 is a exploded view of a type of boring-tool guide assembly; and

FIG. 4 is a back perspective view of an alternate boring-tool guide.

DESCRIPTION OF THE PREFERRED EMBODIMENT

Referring now to the drawing, there is shown an embodiment of the surgical deflector and drilling guide 10 which is constituted by a S-shaped, ribbon-like main body main body 11. The upper end of the main body 11 expands into a generally triangular head 12. The handle is slightly convex and has an opening 13 along the upper edge which is shaped and dimensioned to allow the insertion of four fingers.

The lower end of the device forms a positioning foot 14. The lower edge of the foot has a concavely arcuate area 15 which is serrated with a plurality of teeth 16 designed to anchor the tool on a boney tissue. As shown in FIG. 1, the device can be positioned against the head 17 of a patient's femur 18 after having been inserted through an incision cut into the gluteus medius. With the foot 14 inserted through the incision up to the shank 19 until the foot is firmly anchored on the head 17 of the femur, the surgeon can push the handle 12 against the hip of the patients in order to deflect any tissue which could interfere with a good access to the work area. In this illustrative example, the task of the surgeon is to bore an axial hole for insertion of a supporting pin into the femur starting at the point 20 marked with a cross on the drawing. A boring-tool guide assembly 21 is attached to the foot 14 of the tool just above the serrated edge. The boring-tool guide assembly comprises a sleeve 22 having a T-shaped nib 23 which can detachably be inserted into a corresponding bracket 24 which is permanently mounted against the tool 10. The surgeon can thus insert the tip of a drill bit, awl, reamer or any other boring tool into the sleeve 21 to obtain a perfect aim toward the boring target 20. A small clip 25 is affixed above the boring guide assemby 21 and can be used to mount the end of a miniature light fixture and direct its beam toward the work area 20.

Shown in FIG. 4, is an alternate embodiment 26 of the boring-tool guide which has a similar nib 23 and can be substituted for the sleeve 22.

It should be understood that the described embodiment could be used in other areas of a patient's anatomy to provide clear access to any part of a boney tissue which requires attention.

While the preferred embodiment of the invention has been described, other similar tools could be devised and modifications could be made without departing from the spirit of the invention and the scope of the appended claims.

What is claimed is:

1. A surgical deflector and boring tool positioner to facilitate access to a patient's internal tissue which comprises:
  a generally S-shaped, ribbon-like main body;
  the upper part of said body expanding into a generally triangular handle, and the lower part defining a positioning foot having a concavely arcuate end dimensioned to ride above the head of the patient's femur; and
  means for guiding a boring tool into the boney tissue, wherein said means for guiding including a sleeve mounted above said arcuate end and axially directed toward the boney tissue.

2. The device claimed in claim 1, wherein said means for guiding includes a bracket permanently attached to the positioning foot and detachably mounting said sleeve.

3. The device claimed in claim 1 which further comprises a clip attached to said main body above said means for guiding, and being shaped and dimensioned to hold a miniature light fixture directed toward said positioning foot.

* * * * *